United States Patent [19]
Gupta et al.

[11] Patent Number: 6,090,993
[45] Date of Patent: Jul. 18, 2000

[54] PROCESS FOR THE PREPARATION OF AROMATIC SOLVENT FROM A DIOXANE CONTAMINATED AROMATIC STREAM

[75] Inventors: Anurag Ateet Gupta; Suresh Kumar Puri; Arunagiri Samy; Arvind Pratap Singh; Biswajit Basu; Som Prakash Srivastava; Akhilesh Kumar Bhatnagar, all of Faridabad, India

[73] Assignee: Indian Oil Corporation Ltd., Mumbai, India

[21] Appl. No.: 09/178,581

[22] Filed: Oct. 26, 1998

[51] Int. Cl.$^7$ ................................. C07C 7/12; C07C 7/13
[52] U.S. Cl. ................ 585/827; 585/820; 585/824; 585/826
[58] Field of Search ...................... 585/820, 824, 585/826, 827

[56] References Cited

U.S. PATENT DOCUMENTS

| | | | |
|---|---|---|---|
| 3,007,980 | 11/1961 | Barton et al. | 585/824 |
| 3,121,756 | 2/1964 | Barrer | 585/827 |
| 3,398,208 | 8/1968 | Ward | 585/824 |

*Primary Examiner*—Walter D. Griffin
*Attorney, Agent, or Firm*—Venable; George H. Spencer; Ashley J. Wells

[57] ABSTRACT

A process for preparing benzene containing less than 1 ppm (wt) dioxane from an aromatic stream containing benzene which is contaminated with dioxane, the process including providing an aromatic stream containing benzene which is contaminated with dioxane; subjecting the aromatic stream to liquid phase adsorption by contacting an adsorbent contained in at least one column, which adsorbent comprises at least one substance selected from the group consisting of molecular sieves and clay; and recovering benzene containing less than 1 ppm (wt) dioxane. Preferably, the liquid phase adsorption is carried out at a pressure ranging from atmospheric pressure to 20 kg/cm$^2$ and at a temperature ranging from ambient temperature to 50° C. Preferably, the molecular sieves have a pore size of 10 Å. The process may further include regenerating the adsorbent by passing a flow of nitrogen gas through the adsorbent at a temperature ranging from 200 to 300° C. Alternatively, the process may further include regenerating the adsorbent by heating the adsorbent at a temperature ranging from 200 to 300° C. for a period of time which is effective to regenerate the adsorbent.

5 Claims, No Drawings

PROCESS FOR THE PREPARATION OF AROMATIC SOLVENT FROM A DIOXANE CONTAMINATED AROMATIC STREAM

BACKGROUND OF THE INVENTION

1. Field of the Invention

The present invention relates to a novel process for the production of pure aromatic solvents. In particular, the invention relates to a process for the production of pure aromatic solvents from dioxane contaminated aromatic streams. More particularly, the invention relates to a process for the production of Detal grade benzene from aromatic streams of the Udex process.

2. Background of the Related Art

The aromatic rich stream employed in the process of the invention is that which is left behind after the recovery of raffinate from naphtha reformate. The Udex plant feed, as reformied naphtha received from a Catalytic Reforming Unit (CRU), is drawn from the Udex charge storage tanks and is provided with gas blanketing to prevent contamination from air.

The aromatic rich feed is pumped and introduced into a counter current multistage extractor column typically at a $40^{th}$ tray, after having been preheated to 120–130° C. by exchanging heat with the raffinate and with hot oil in the preheater. The feed flow is controlled by a feed rate controller. The extractor column has 60 perforated trays.

The solvent, aqueous Tetra Ethylene Glycol (TTEG), which is essentially immiscible with the non-aromatic hydrocarbons of the feed is drawn from the bottom of a stripper column and is pumped to the upper section of the column at 120–130° C. after being heat exchanged with stripping water. The solvent flow is controlled by a feed rate controller.

The raffinate, almost free of aromatics, is withdrawn from the top of the extractor and sent to a first stage settler after being heat exchanged with the feed and cooler water. From the first stage settler, it is sent to a second stage settler for further water washing and subsequently to a storage tank.

The aromatic rich solvent is withdrawn from the bottom of the extractor. Extractor pressure is set to maintain the hydrocarbon below its bubble point which is controlled by a split range controller at 6–7 kg/cm$^2$. The rich solvent is introduced into a flash drum section of a column by a pressure gradient at 120–130° C. through a flow controller. The flash drum operates at 2.0 to 2.5 kg/cm$^2$ pressure. In this flash drum, hydrocarbon light ends escape together with most of the light aliphatic hydrocarbons which are subsequently condensed and received in a suitable vessel. From the stripper receiver, the condensed light ends are recycled back to the bottom section of the extractor column for further recovery of aromatics. The bottoms from the flash drum flow to the stripper section of the column where heat is supplied at the bottom by a hot oil reboiler. Bottom temperature is controlled at 140–150° C. The aromatic stripping from the rich solvent is carried out and facilitated by the water which is pumped from a water receiver at the $39^{th}$ tray in the form of steam and, at the bottom, in the form of water. Some aromatics leave the top of the stripper as vapor while the aromatic (extract) is drawn as a side stream from the $25^{th}$ tray which, after condensation, goes to the extract receiver. The condensed aromatics, thereafter, are water washed. The washed extract flows to a clay tower feed storage tank after being pressure controlled for clay treatment and fractionation.

The stripper solvent is withdrawn as bottoms from the stripper column and returned to the extractor column. A slip stream of this solvent is preheated to around 200° C. by hot oil. The regenerator bottom temperature is controlled at around 200° C. The solvent vapors from the top are condensed and pumped back to the bottom of the column. A certain amount of sludge accumulates at the bottom of column which is drained out during shutdown.

The aromatic extract from the extraction section is routed to a buffer tank from which it is pumped to the clay tower after being preheated with clay tower bottoms and a hot oil preheater to 160–220° C. One of the clay towers is used at a time.

The clay towers are packed with 10 MT of DCM or Korvi clay (30 to 60 mesh) having de-coloring properties. The clay treatment removes trace quantities of olefins and diolefins so as to meet the acid wash color specification for nitration-grade benzene and toluene. If the acid wash color of the out going product is no longer satisfactory, the extract will be sent through other clay towers, while the former clay tower is emptied out and loaded with a fresh charge of clay.

Clay tower pressure is controlled at 20–23 kg/cm$^2$ to keep the extract in the liquid phase to obtain the maximum decolorizing efficiency by the clay treatment.

The decolorized product after the heat exchange with feed enters the benzene column at around 90–100° C. at the $41^{st}$ tray. Hot oil flow to the reboiler is adjusted to maintain bottom temperature at 142° C. Tray $41^{st}$ and $49^{th}$ temperatures are maintained at around 95–100° C. and 128–130° C., respectively. These settings are essential to know the flooding condition of the column. The column top temperature is maintained at 89–92° C. and the top pressure is maintained at 0.3 kg/cm$^2$.

Column overhead vapors are condensed and received in a receiver from which settled water is drained out of a water booth and hydrocarbons are pumped as reflux which is suitably cascaded with level controllers. A drag stream is withdrawn from the pump discharge and recycled back to the stripper overhead condenser after passing through a drag stream cooler and a drag stream settler to keep the concentration of non-aromatics in the benzene to a tolerable limit.

Benzene product is withdrawn as a liquid side cut from the $7^{th}$ tray which is cascaded with a differential temperature controller which maintains a differential temperature in the range of 2.5 to 3.0° C. between tray 14 or 18 and tray 4. A selector switch is provided for selecting either tray 14 or 18. Benzene run down is sent to intermediate storage by a pump after cooling.

The run down benzene samples were analyzed using gas chromatography for dioxane content as per UOP-92 1. The analysis showed that all of these benzene samples were contaminated with dioxane and not suitable for producing Linear Alkyl Benzene (LAB) in the Detal unit. Pure benzene having a dioxane content less than 1 ppm is useful in the Detal process for making LAB, a surfactant intermediate.

Since dioxane has a boiling point close to that of benzene and the geometry of both of these molecules are quite similar, it is rather impossible to achieve efficient yet economic separation of dioxane at this level by distillation.

The specification of benzene suitable for the Detal process is summarized in Table-1 which indicates, along with ASTM D-4734, UOP's specification requirements which are more stringent than those of the ASTM specification.

TABLE 1

Benzene Specifications for the Detal Unit

| PROPERTY | SPECIFICATION | METHOD |
| --- | --- | --- |
| Benzene, wt % | 99.90 Min | ASTM D-4492 |
| Sulfur, wt ppm | 1.0 Max | ASTM D-4045 or UOP-304 |
| Thiophene, wt ppm | 0.5 Max (*) | ASTM D-1685 of D-4735 |
| Toluene, wt % | 0.05 Max | ASTM D-4492 |
| Nonaromatic Hydrocarbons, wt % | 0.10 Max | ASTM D-4492 |
| Acid Wash Color | Pass with 1 Max | ASTM D-848 |
| Acidity | Not Detectable | ASTM D-847 |
| Copper Corrosion | Pass (1a or 1b) | ASTM D-849 |
| Color, Pt-Co Scale | 20 Max | ASTM D-1209 |
| Relative Density, 15.56/15.56° C. | 0.8820–0.8860 | ASTM D-3505 |
| Distillation range, ° C. | 1.0 Max | ASTM D-850 |
| Solidification point, ° C. | 5.45 Min | ASTM D-852 |
| Total nitrogen, wt ppm | 0.3 Max (*) | UOP-385 |
| p-Dioxane, wt ppm | 1.0 (*) | UOP-921 |

(*) Indicates a UOP specification in addition to or more stringent than the ASTM specification.

Detal grade benzene is conventionally produced by a sulfolane extraction process. Most present day solvent extraction units are based on solvents, such as sulfolane and pyrrolidine based solvents, which can control successfully the dioxane content of the benzene obtained from straight run naphtha to the desired limits. No method has been reported so far which can successfully control the dioxane content in benzene using TTEG as extractant.

An object of the invention is to propose a process for the production of dioxane free benzene.

Another object of the invention is to propose a process for the production of dioxane free benzene utilizing optimum operating conditions of pressure, temperature and feed flow rate for an adsorption unit under plant hydrodynamic conditions.

Yet another object of this invention is to propose a process for the production of dioxane free benzene utilizing the capacity of molecular sieves and clays for the removal of dioxane from aromatic rich streams.

SUMMARY OF THE INVENTION

According to this invention there is provided a process for preparation of benzene containing less than 1 ppm dioxane from dioxane contaminated aromatic streams of the kind such as herein described which comprises subjecting said aromatic stream to a liquid phase adsorption in at least one column containing molecular sieves as an adsorbent.

In accordance with the present invention, there is provided a process for the production of pure aromatic solvent substantially free from dioxane which comprises passing an aromatic rich stream containing dioxane over a column of adsorbent at ambient to elevated temperature and pressure which maintains the hydrocarbon feed in the liquid state, thereby obtaining the desired pure aromatic solvent.

The process of the invention therefore consists of adsorption of dioxane onto the adsorbent thereby resulting in a final product of desired quality which is free from dioxane and meets the relevant product specification.

It has been found that performance of the adsorbents is most optimum in a temperature range of ambient to 50 degrees centigrade and under a superficial velocity of less than 0.1 cm/sec. The operating pressure was atmospheric to 25 kg/cm.$^2$ Adsorbents used in the invention are as follows: (i) molecular sieves, and (ii) clays. Molecular sieves used in the invention are selected with a 10 Å pore size (Table 2). Clays used in the invention are commercially available FILTROL 24 of M/s. Harshaw-Filtrol, USA and TONSIL of Sud Chemie, Germany (Table 3). These adsorbents are either used singularly or in combination with varied proportions. Regeneration of any of these adsorbents is accomplished using nitrogen flow at elevated temperatures or heating the adsorbent as such at temperatures ranging from 200–300° C.

TABLE 2

Characteristics of Molecular Sieves

| S. NO | CHARACTERISTICS | TYPICAL PROPERTIES |
| --- | --- | --- |
| 1. | Pore Dia, Å | 10 |
| 2. | Alkali Metal | Sodium |
| 3. | Bulk Density, g/l | 530 Min |
| 4. | Bed Crushing Strength Value, % | 75 Min |
| 5. | Loss on Attrition, % | 0.2–0.5 |
| 6. | Crush Strength | 3.5–6.0 kg |

TABLE 3

Characteristics of Clay

| | | Typical Data | |
| --- | --- | --- | --- |
| S. NO | CHARACTERISTICS | Clay 1 | Clay 2 |
| 1. | Moisture (% wt. Loss at 105° C.) | 12 | 12 |
| 2. | Residual Acidity, mg KOH/g | 8.5 | 16 |
| 3. | Particle Size, Type Standard Sieve | | |
| | i) Passing 20 mesh, wt % | 70 | 85 |
| | ii) Passing 60 mesh, wt % | 5 | 5 |
| 4. | Bulk Density, g/l | 740 | 750 |
| 5. | Surface Area, (BET), m$^2$/g | 425 | 350 |
| 6. | Effective Particle Size (Cal.) mm | 0.48 | 0.48 |
| 7. | Void Fraction (Packed) | 0.32 | 0.32 |
| 8. | Total Pore Volume, cc/g (Mercury Porosimeter) | 0.198 | 0.176 |

The useful life of adsorbents under the conditions of the experiments carried out was found to be quite large as adsorbent regeneration with nitrogen gas at 200–300° C., or simple heating at 200–300° C. provides an adsorbent with a similar efficiency as that of fresh adsorbents.

The invention is described as follows:

An aromatic feed containing dioxane is pumped to the adsorbent bed. The feed comes in contact with adsorbents where due care is taken to avoid channeling. Dioxane present in the feed gets adsorbed on the active sites of adsorbent sieves thereby reducing the overall concentration of dioxane to the desired level.

The treated aromatic stream is withdrawn and pumped to the storage facilities. On saturation of the adsorption bed, heated nitrogen gas (200–300° C.) is passed through the adsorbent bed while the feed flow is diverted to the other column containing a similar type and quantity of adsorbent.

DESCRIPTION OF THE PREFERRED EMBODIMENTS

The invention will now be illustrated with the help of the following examples:

EXAMPLE 1

A 200 ml sample of benzene having a dioxane content of 100 ppm was contacted with 10 g of activated molecular sieves for 60 minutes in batch mode at an ambient temperature and pressure at a fixed RPM of 60 using a reactor of one liter capacity. Treated product was found to contain a highly reduced dioxane content of <1 ppm.

EXAMPLE 2

A sample of a benzene fraction having a dioxane content of 100 ppm was passed through a column packed with molecular sieves which was maintained at ambient temperature and pressure conditions. The quantity of molecular sieve of Type 1 packed was 100 grams. The flow rate of the feed was 180 ml. per hour. The effluent was analyzed and the dioxane content was found to be less than 1 ppm.

EXAMPLE 3

The same experiment was performed as described in example 2 but the adsorbent was changed to Clay 1. The effluent contained less than 1 ppm dioxane.

EXAMPLE 4

The same experiment was performed as described in example 2 but the adsorbent was changed to Clay 2. The effluent contained less than 1 ppm dioxane.

EXAMPLE 5

A sample of benzene having a dioxane content of 100 ppm was passed through a column containing 100 grams of molecular sieves of Type 1 maintained at 50 degrees centigrade at a pressure of 20 kg/cm$^2$. The feed flow was controlled at 180 ml per hour. The effluent had a dioxane content of less than 1 ppm.

EXAMPLE 6

The same experiment was performed as described in example 5 but the adsorbent was changed to Clay 1. The effluent contained less than 1 ppm dioxane.

EXAMPLE 7

The same experiment was performed as described in example 5 but the adsorbent was changed to Clay 2. The effluent contained less than 1 ppm dioxane.

EXAMPLE 8

The experiment was set up as in example 2. The feed flow was varied from 150 to 300 ml/hour to observe the effect of superficial velocity on the dioxane content. From the dioxane analysis of the effluent product of the reactor, a superficial velocity of 0.01 cm/sec to 0.1 cm/sec was found suitable for the use of all types of adsorbents.

EXAMPLE 9

The experiment was set up as in example 2. The feed flow was continued for 100 hours. The dioxane content of the resultant effluent was found to increase with time uniformly and could be brought down suitably by adjusting the flow rate of the benzene sample.

EXAMPLE 10

The experiment was set up as in example 2. A benzene sample from a UDEX unit was taken into a bed of molecular sieve of Type 1 maintained at an initial ambient temperature and pressure. The feeding was continued until the effluent dioxane content of >1 ppm was reached. The bed temperature was raised by 5 degrees centigrade and the feeding continued while holding the effluent dioxane content below 1 ppm. This procedure continued until the bed temperature reached 50 degrees centigrade. The composite effluent thus collected had a dioxane content of less than 1 ppm.

EXAMPLE 11

The same experiment was performed as described in example 10 but the molecular sieves were changed to Clay 1. The effluent contained less than 1 ppm dioxane.

EXAMPLE 12

The same experiment was performed as described in example 10 but the molecular sieves were changed to Clay 2. The effluent contained less than 1 ppm dioxane.

We claim:

1. A process for preparing benzene containing less than 1 ppm (wt) dioxane from an aromatic stream containing benzene which is contaminated with dioxane, the process comprising:

providing an aromatic stream containing benzene which is contaminated with dioxane;

subjecting the aromatic stream to liquid phase adsorption by contacting an adsorbent contained in at least one column, which adsorbent comprises at least one substance selected from the group consisting of molecular sieves and clay; and recovering benzene containing less than 1 ppm (wt) dioxane.

2. The process as claimed in claim 1, wherein the liquid phase adsorption is carried out at a pressure ranging from atmospheric pressure to 20 kg/cm$^2$ and at a temperature ranging from ambient temperature to 50° C.

3. The process as claimed in claim 1, wherein the molecular sieves have a pore size of 10 Å.

4. The process as claimed in claim 1, further comprising regenerating the adsorbent by passing a flow of nitrogen gas through the adsorbent at a temperature ranging from 200 to 300° C.

5. The process as claimed in claim 1, further comprising regenerating the adsorbent by heating the adsorbent at a temperature ranging from 200 to 300° C. for a period of time which is effective to regenerate the adsorbent.

* * * * *